United States Patent
Landis et al.

(10) Patent No.: US 7,191,784 B2
(45) Date of Patent: Mar. 20, 2007

(54) DENTAL FLOSSER WITH FLOSS BEADS

(76) Inventors: Timothy J. Landis, 6015 Alta Loma Pl., Granite Bay, CA (US) 95764; Victoria Landis, 6015 Alta Loma Pl., Granite Bay, CA (US) 95764

( * ) Notice: Subject to any disclaimer, the term of this patent is extended or adjusted under 35 U.S.C. 154(b) by 0 days.

(21) Appl. No.: 11/049,367

(22) Filed: Feb. 1, 2005

(65) Prior Publication Data

US 2005/0217693 A1 Oct. 6, 2005

Related U.S. Application Data

(60) Provisional application No. 60/541,558, filed on Feb. 3, 2004.

(51) Int. Cl.
*A61C 15/00* (2006.01)
(52) U.S. Cl. ...................................... 132/323
(58) Field of Classification Search ............... 132/323, 132/327, 326
See application file for complete search history.

(56) References Cited

U.S. PATENT DOCUMENTS

| 2,180,522 | A | * | 11/1939 | Henne | 132/323 |
|---|---|---|---|---|---|
| 3,417,752 | A | * | 12/1968 | Butler | 606/147 |
| 5,881,745 | A | * | 3/1999 | Landis | 132/323 |
| 5,931,171 | A | * | 8/1999 | Landis et al. | 132/323 |
| 5,975,296 | A | * | 11/1999 | Dolan et al. | 206/368 |
| 6,085,760 | A | * | 7/2000 | Chodorow | 132/323 |

* cited by examiner

*Primary Examiner*—Cary E. O'Connor
(74) *Attorney, Agent, or Firm*—John P. O'Banion

(57) ABSTRACT

A dental flossing apparatus having a body with extending retention arms configured for retaining a length of dental floss under tension between the arms. The tension is applied between resilient arms and biased into tension by means of legs coupled to said arms which are manipulated and optionally locked together. By way of example, a bore extending into the bead may be engaged over a post extending proximal the end of the retention arms. Other forms of engaging the floss with the ends of the retention arms are also described. The body of the flossing device or the beads may be configured in the shape of animals, action figures, characters, or other objects to enhance entertainment value. Floss for the flossing device comprise short sections of floss with a bead near each end, which may be separated from a roll of floss upon which a plurality of beads are affixed.

20 Claims, 14 Drawing Sheets

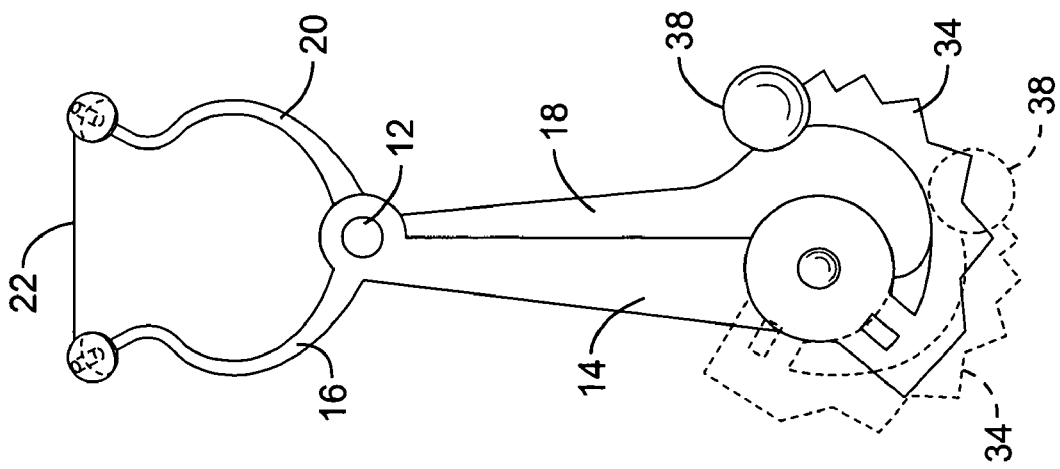
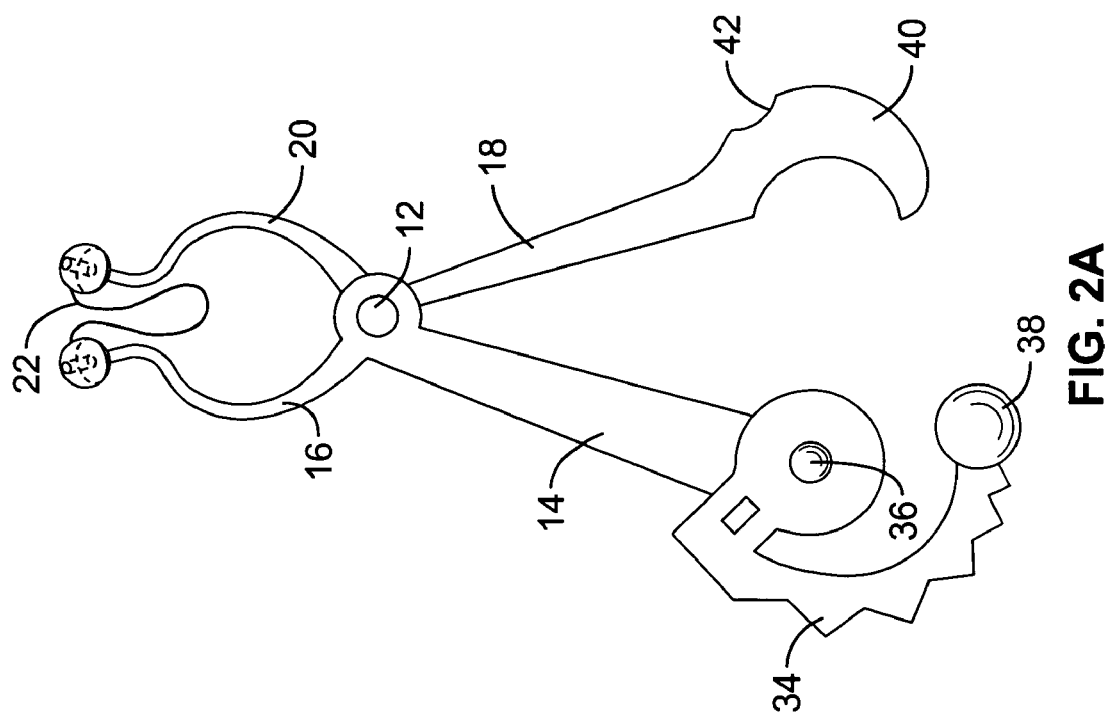

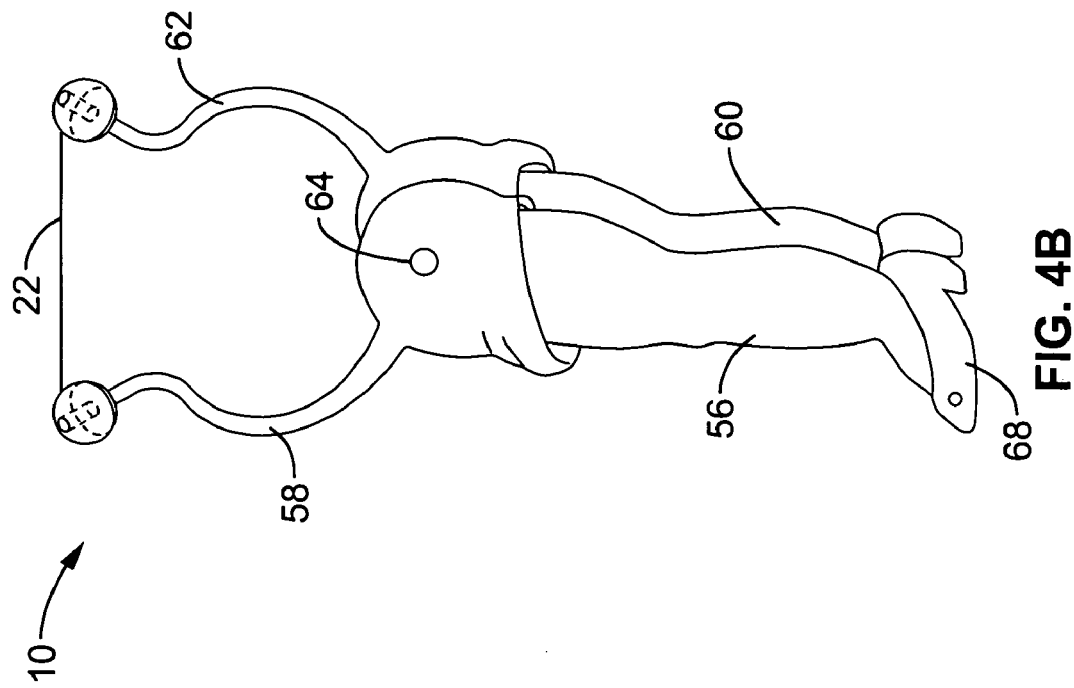
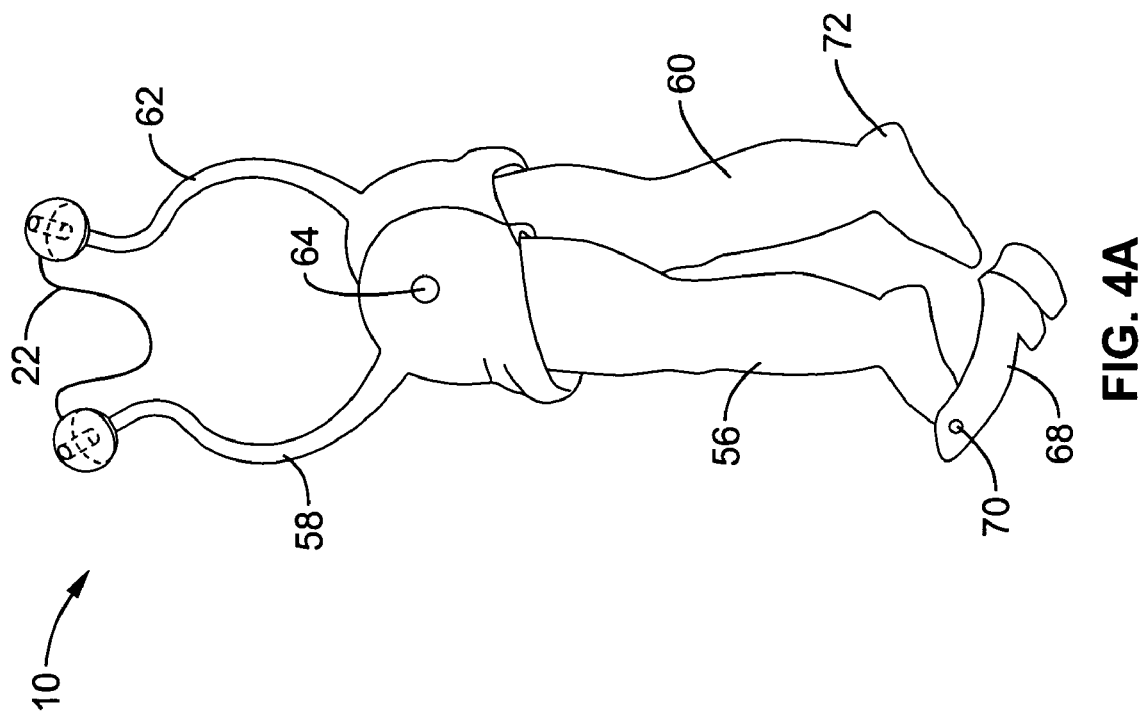

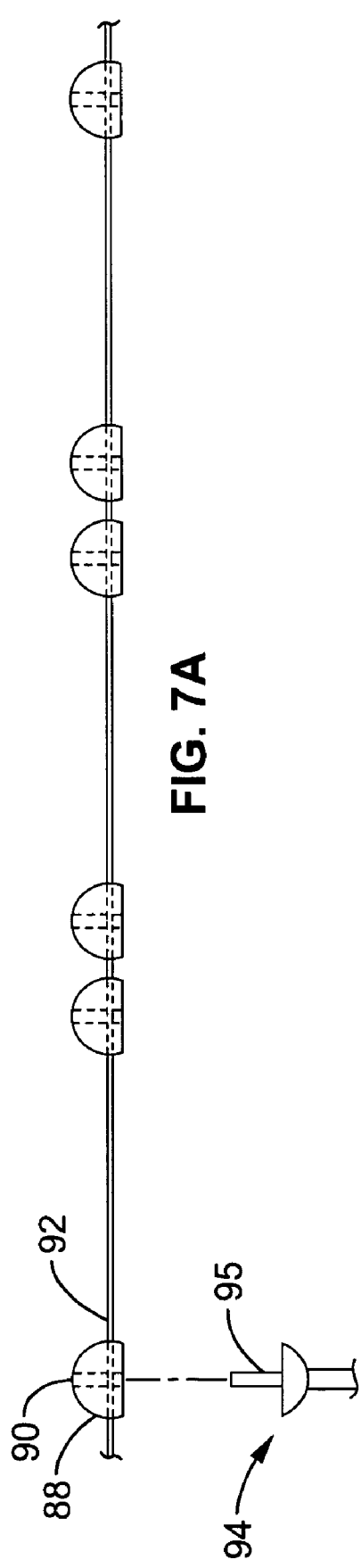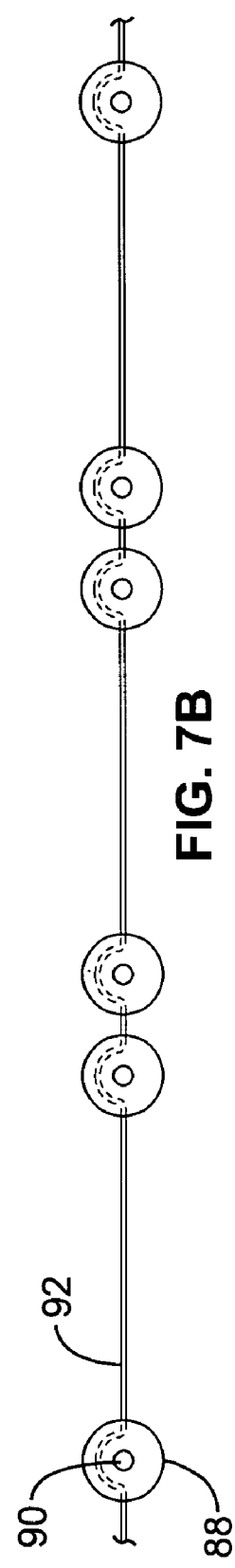
FIG. 7A
FIG. 7B

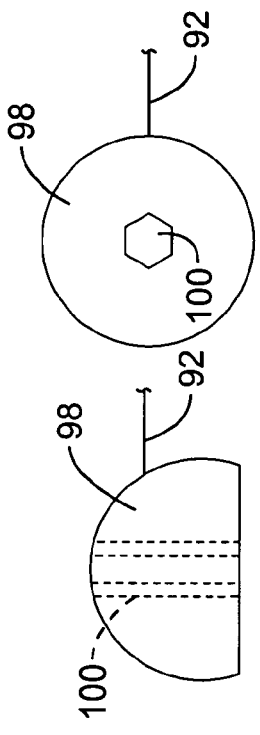
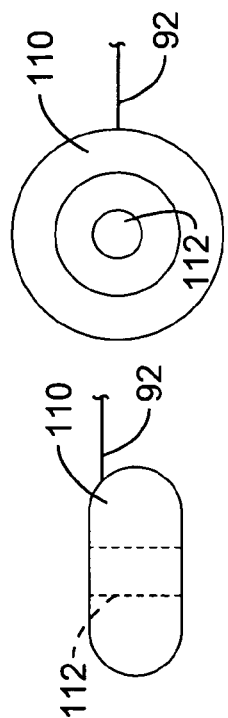
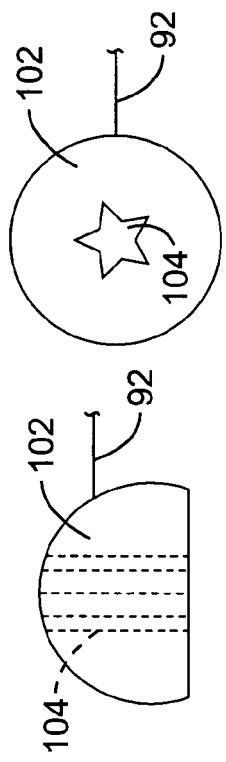
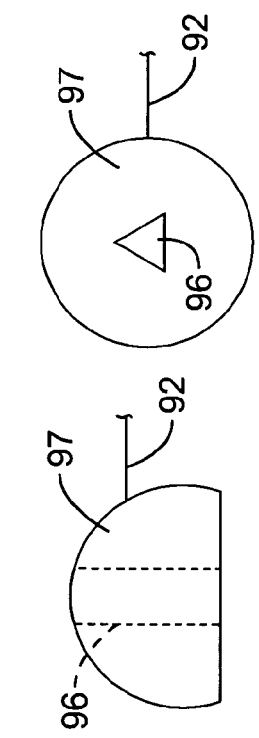
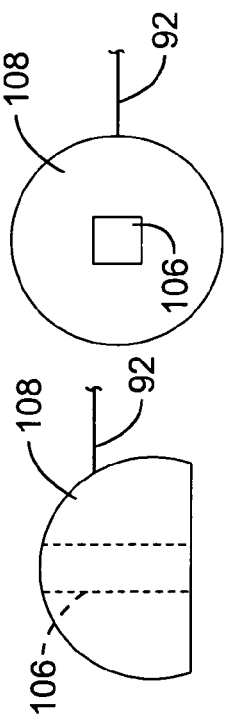

DENTAL FLOSSER WITH FLOSS BEADS

CROSS-REFERENCE TO RELATED APPLICATIONS

This application claims priority from U.S. provisional application Ser. No. 60/541,558 filed on Feb. 3, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This application pertains generally to dental hygiene products and more particularly to a hinged floss handle with beaded dental floss for flossing teeth.

2. Description of Related Art

The removal of food particles and plaque from between the teeth is an important part of good oral hygiene because these particles may not be removed with brushing alone. Dental flossing is an effective method for removing matter from between teeth.

Flossing is an often unpleasant but necessary routine. The conventional method for flossing teeth involves grasping opposite ends of a length of dental floss with each hand, and manually manipulating the floss back and forth between the teeth. Anyone who has performed this task is well aware that the nature of dental floss inherently makes it difficult to securely grasp and tautly hold a tensioned strand of floss while maneuvering and manipulating the suspended section between all the teeth. Because dental floss is intentionally smooth to ease its movement between teeth, it is difficult for the user to obtain a secure grip. It is often necessary to create tension in the length of dental floss to facilitate the placement of the floss between the teeth. Consequently, the ends of the floss are typically wrapped around the fingers of the user to maintain tautness.

Those who have flossed in this conventional manner have experienced the discomfort that accompanies fingers that are tightly wrapped with floss. Often the wrapped fingers turn purplish and begin to numb due to a lack of blood flow. If skin is soft, such as after showering or bathing, some low friction flosses (i.e. Glide) will cut the fingers. Such inconveniences and difficulties spurred the development of various devices to hold the dental floss while teeth flossing. For example, one device developed to alleviate such problems provides short sections of floss with stub sections or gripper handles at both ends of the floss section.

Another device that was developed to hold dental floss included a pair of sleeves fitted over the index fingertips of each hand. One sleeve served as the supply sleeve containing pre-wound floss, and the other sleeve served as the take-up sleeve for receiving spent floss. To floss, both fingers with the sleeves are required to be inserted into the mouth with a section of floss suspended between the sleeves to allow the user to floss between the teeth. Tension is provided to the floss by the fingers of each hand drawing each end of the floss in opposite directions.

One problem common to both of the foregoing flossing devices is that at least one finger from both hands must be inserted into the mouth, especially when flossing between the rear molars. This often proves to be unwieldy and cumbersome as the mouth must be fully opened to allow insertion of the fingers therein.

A further problem which has not been fully appreciated in the art is that of encouraging individuals to regularly floss their teeth, both adults and children.

Accordingly, there is a need for a low cost, dental flosser that can floss teeth without requiring the placement of the fingers of the user into the mouth and is capable of exerting tension on the floss for easy disposition of the floss between teeth. The present invention satisfies this need, as well as others, and overcomes the deficiencies found in the prior art.

BRIEF SUMMARY OF THE INVENTION

The present invention is a dental flossing device with a handle and two arms configured with receptacles for engaging beads located along a section of dental floss. The flossing device applies tension to the dental floss and allows placement of dental floss between teeth during dental examinations or personal cleaning procedures.

In one embodiment of the invention the dental flossing device comprises a hinged apparatus with articulating legs and tension arms and a length of dental floss extending between the distal tips of the tension arms. The dental floss is preferably provided with regularly spaced beads that have holes (bores) that are configured to fit on a corresponding post on the tip of each tension arm. The posts and corresponding holes in the floss beads can have virtually any geometric or non-geometric shape. Alternatively, the floss beads may be configured to include a post or posts that are disposed in corresponding holes or receptacles in the tension arms. It should also be appreciated that any convenient mechanism for securing the beads, or similar securement structures located at the ends of a section of dental flow, may be utilized without departing from the teachings of the present invention.

In use, the ends of a length of dental floss are secured to the tips of the two tension arms, preferably through the coupling of floss beads with receptacles on the arm tips. One embodiment of the apparatus preferably has the opposite of a scissor like action such that the tension arms and tips are drawn apart when the legs are brought together from an open to a closed position. Using legs and arms that do not cross at the pivot point (each leg and attached arm remain on their respective sides of the pivot point) it can be seen that the movement of the legs about the pivot point will cause the distal tension arms to move in an opposing direction thereby creating tension or slack in a section of dental floss coupled to the tips of the arms. It should also be appreciated that other articulation mechanisms can be adopted which spread the floss retention arms in response to closing the legs of the floss holder device.

A locking mechanism is preferably provided to secure the legs together to maintain the tension in the length of dental floss and to provide a handle for the user.

The section of dental floss retained across the tips of the tension arms is used to floss between the teeth. It is often desirable to apply tension to the section of dental floss when placing the floss between teeth. Increased tension on the dental floss facilitates the placement and removal of the dental floss between teeth.

The invention provides numerous beneficial aspects for teeth flossing, a partial list of these aspects is outlined below.

An object of the invention is to provide a dental floss apparatus that eases dental flossing by relieving the discomfort of wrapping dental floss around the fingers.

Another object of the invention is to provide a reusable dental floss apparatus that is inexpensive and easy to manufacture.

Another object of the invention is to provide dental floss that is adapted to be fixed on the ends of arms of flossing devices.

Another object of the invention is to provide a dental floss apparatus that is configured to exert tension on a section of dental floss during use.

Still another object of the invention is to provide a dental floss apparatus fabricated into the shape of an entertaining character to encourage flossing by children.

An embodiment of the invention is an apparatus for flossing teeth, comprising first arm having a first tip, second arm coupled to the first arm with a second tip retained at a predetermined separation from the first tip, handle joining the first arm and the second arm, and means for reversibly coupling a length of dental floss between the first and second arms under sufficient tension for being manipulated between the teeth of an individual during flossing.

An aspect of the invention is where the handle is configured in the shape of an animal, character, action figure or object.

Another aspect of the invention is where the handle comprises a first leg joined to the first arm, a the second leg joined to the second arm, and a pivot which joins the first leg to the second leg.

A further aspect of the invention is where moving the first leg and the second leg toward one another through the pivot increases the distance between the tips of the first arm and the second arm and is configured for applying tension to a section of floss retained between the first and the second arms.

A still further aspect of the invention is a means for locking the first leg to the second leg to retain the tension on the section of floss between the first and the second arms.

Another aspect of the invention is where the means for locking comprises a lock configured to slidably engage along at least a portion of the length of the first leg and the second leg, or a clasp coupled to one leg and configured to engage the opposing leg.

A further aspect of the invention is where the means of reversibly coupling a section of dental floss comprises engagement structures located toward the ends of the first arm and the second arm, and where each the engagement structure is configured for engaging a complementary bead structure retained along the length of an elongated section of dental floss.

A still further aspect of the invention is where the engagement structure and the complementary bead structure comprise post and bore structures where the post is engaged through the bore, where the bead is configured with a bore which is engaged over a post extending from the arm, or the bead is configured with a post which is engaged within a bore on the arm.

Another aspect of the invention is where the engagement structure and the complementary bead structure comprises ball and socket structures, and where the ball, located along a length of dental floss, is engaged within the socket on the end of the arm.

A further aspect of the invention is where the engagement structure and the complementary bead structure are configured in a nested arrangement, and where the bead is slidably engaged within either the interior or over the exterior of a portion of the arm.

Another embodiment of the invention is an apparatus for flossing teeth, comprising first leg, first arm extending from the first leg, a second leg pivotally coupled to the first leg, a second arm extending from the second leg, and means for reversibly coupling a length of dental floss for retention between the first and second arms under sufficient tension, applied by drawing the first and the second legs toward one another, for being manipulated between the teeth of a user during flossing.

Another aspect of the invention is where the means for reversibly locking the first leg with the second leg comprises a clasp coupled to the first leg, where the clasp is configured to engage and prohibit the pivotal movement of the second leg.

A further aspect of the invention is where the clasp comprises a clip pivotally coupled to the first leg, and where the clip is configured to frictionally engage the second leg toward prohibiting the movement of the second leg.

A still further aspect of the invention is where the clip further comprises a structure configured to frictionally engage a corresponding structure in the second leg.

Another aspect of the invention is where the clip further comprises a magnet coupled to the clasp and configured to reversibly couple the clip to an object having iron metal.

A further aspect of the invention is where the means for reversibly coupling the length of dental floss comprises at least a first bead and second bead coupled to a length of dental floss, and means for reversibly coupling each the bead with each the arm of the apparatus.

A still further aspect of the invention is where the means for reversibly coupling the bead to the arm comprises a post mounted to the tip of the arm and configured of a size and shape to be disposed within a bore within the bead.

Another aspect of the invention is where the posts are configured having a non-circular cross section which restricts the rotation of the beads around the posts.

A further aspect of the invention is annular ridges disposed at the distal portions of the post to prevent inadvertent disengagement of the bead from the post.

A still further aspect of the invention is where the means for reversibly coupling the bead to the arm comprises a post extending from the bead configured of a size and shape for being received within a bore proximal to the tip of the arm.

A yet further aspect of the invention is where the posts have a cross-section selected from the group of shapes consisting of circles, ovals, triangles, trapezoids, squares, rectangles, polygons, pentagons, hexagons, heptagons, octagons, star, heart, crescent or a cross.

Another aspect of the invention is where the means for reversibly coupling each the bead with each the arm comprises shaped bead joined along a length of dental floss, and a notch proximal the tip of the arm configured for receiving the shaped bead.

A further aspect of the invention is where the means for reversibly coupling each the bead to each the arm comprises a shaped bead joined to a length of dental floss, and a socket proximal the tip of the arm configured to receive the shaped bead, where the socket is shaped as an open frustoconical sleeve, and where the socket is configured with a slot through which the dental floss may be passed for aligning the shaped bead with the interior of the socket.

A still further aspect of the invention is where the means for reversibly coupling each the bead to each the arm comprises at least a first and second bead coupled to a length of dental floss, and a spherical tip proximal each the arm configured to frictionally engage each the bead.

Another embodiment of the invention is a body, a first resilient tension arm extending from the body, a second resilient tension arm extending from the body, and means for reversibly coupling a length of dental floss under tension proximal the ends of the first and second arms.

A further aspect of the invention is where the means for reversibly coupling the length of dental floss comprises a receptacle proximal the ends of the tension arms which is configured for engaging beads located along a length of dental floss.

Another aspect of the invention is where the receptacle on the tension arm comprises a post configured of a size and shape for being disposed within a bore extending into or through the bead.

A further embodiment of the invention is dental floss for flossing between teeth, comprising a length of dental floss, and at least two beads disposed on the length of dental floss, where the beads are configured for engaging receptacles proximal the ends of floss retention arms within a flossing device.

Another aspect of the invention is where a plurality of the beads are disposed along the length of the dental floss and configured for being separated into a segment of dental floss having one the bead proximal each end.

A further aspect of the invention is where the beads are configured in a shape selected from the group of shapes consisting of a heart, a tooth, a hand, a fruit, a vegetable, a sports ball, a sports helmet, a knife, a hand grenade, a bomb, or a gun.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2A is a front view of the dental flossing apparatus of FIG. 1, shown in the open and unlocked position.

FIG. 2B is a front view of the dental flossing apparatus of FIG. 2A, shown in the closed and locked position, with a closed but unlocked position shown in phantom lines.

FIG. 4A is a front view of a dental flossing apparatus according to another embodiment of the present invention, showing the hot-legs flosser in the open and unlocked position.

FIG. 4B is a front view of the dental flossing apparatus of FIG. 4A, shown in the closed and locked position.

FIG. 7A is a side view of dental floss with beads affixed thereto according to an aspect of the present invention, shown with a circular central bore through the beads for retention on the flossing arms.

FIG. 7B is a top view of the dental floss with beads of FIG. 7A, showing a semi-circular dental floss path within the beads.

FIG. 8A is a side view of dental floss with beads affixed thereto according to an aspect of the present invention, shown with a triangular central bore through the beads for retention on the flossing arms.

FIG. 8B is a top view of the dental floss with beads of FIG. 8A.

FIG. 9A is a side view of dental floss with beads affixed thereto according to an aspect of the present invention, shown with a hexagonal central bore through the beads for retention on the flossing arms.

FIG. 9B is a top view of the dental floss with beads of FIG. 9A.

FIG. 10A is a side view of dental floss with beads affixed thereto according to an aspect of the present invention, shown with a star-patterned central bore through the beads for retention on the flossing arms.

FIG. 10B is a top view of the dental floss with beads of FIG. 10A.

FIG. 11A is a side view of dental floss with beads affixed thereto according to an aspect of the present invention, shown with a square central bore through the beads for retention on the flossing arms.

FIG. 11B is a top view of the dental floss with beads of FIG. 11A.

FIG. 12A is a side view of dental floss with beads affixed thereto according to an aspect of the present invention, shown with a donut-shaped bead with a central bore through the bead for retention on the flossing arms.

FIG. 12B is a top view of the dental floss with bead of FIG. 12A.

DETAILED DESCRIPTION OF THE INVENTION

Referring more specifically to the drawings, for illustrative purposes the present invention is embodied in the apparatus generally shown in FIG. 1 through FIG. 24. It will be appreciated that the apparatus may vary as to configuration and as to details of the parts, and that the method may vary as to the specific steps and sequence, without departing from the basic concepts as disclosed herein.

Figure 1:
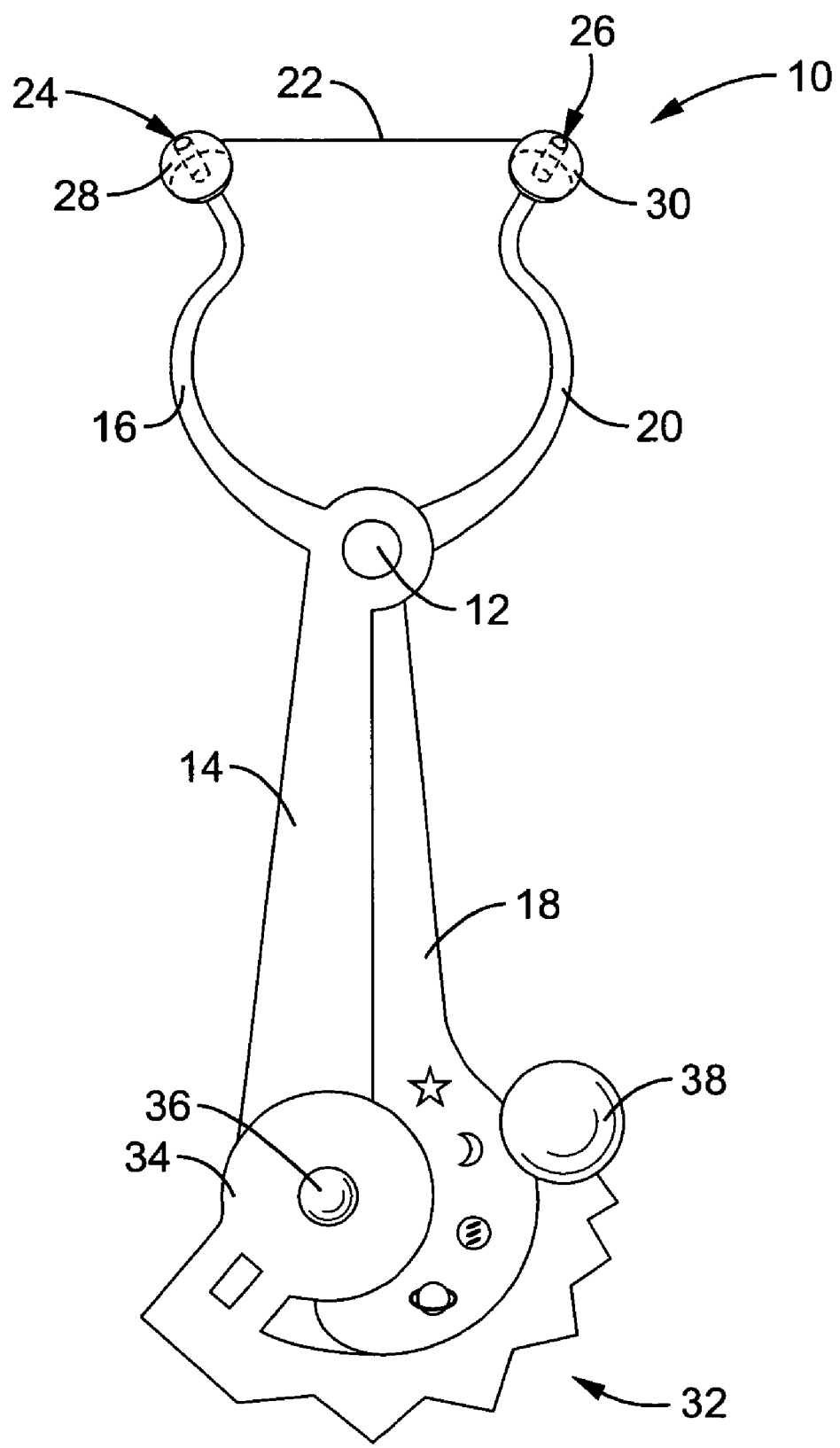
FIG. 1 is a front view of a dental flossing apparatus in accordance with an embodiment of the present invention, shown in the closed and locked position.

Turning first to FIG. 1, FIG. 2A and FIG. 2B, a flossing apparatus 10 in accordance with the present invention is generally shown. The apparatus 10 includes a pivot hinge 12 coupling a first member having a first leg 14 and first arm 16 with a second member having a second leg 18 and second arm 20. Pivot pin 12 can be integral to first leg 14, integral to second leg 18 or an independent piece. A length of floss 22 extends between the tip 24 of first arm 16 and the tip 26 of second arm 20. In the embodiment shown, the length of floss 22 has a bead 28 and a bead 30 on either end with holes configured to fit over the ends of tips 24, 26 of arms 16, 20.

While floss with integral retention structures (beads) are depicted in FIG. 1, it will be understood that other, less preferable, methods known in the art for coupling the ends of the length of dental floss to tips 24, 26 of retention arms 16, 20 may be utilized. For example, the floss may be simply wrapped about tips 24, 26 or the tips may have hooks or holes to secure the ends of the length of floss 22.

It can be seen that the movement of first leg 14 toward second leg 18 about pivot hinge 12 will result in the corresponding movement of first arm 16 away from second arm 20. The movement of the arms 16, 20 creates tension in the length of floss 22 when the legs 14, 18 are brought together. The tension in the length of floss 22 can be increased or decreased by the movement of first and second legs 14, 18.

The apparatus 10 is also preferably provided with an optional locking mechanism 32. By way of example the locking means may comprise a generally arcuate clip 34 that is pivotally connected to first leg 14 with a pivot pin 36. In a preferred embodiment, pivot pin 36 is integral to second leg 14 but can be a separate piece.

As seen in FIG. 2A and FIG. 2B, the rotation of clip 34 about pivot pin 36 brings the spherical end 38 of clip 36 around a shaped end 40 of leg 18 when legs 14, 18 are brought together. The spherical end 38 of clip 36 is disposed in a detent 42 of second leg 18 securely locking legs 14, 18 together and thereby restricting rotation of legs 14, 18 about pivot pin 12 and maintaining tension in the length of floss 22. The locked legs provide a convenient handle whereby the user can maneuver the tensioned floss within the mouth to the proper position for placement between the teeth and for its subsequent removal.

FIG. 2A is an illustration of the open and unlocked position of the apparatus wherein arms 16, 20 are brought toward one another in response to separating legs 14, 18. The open position facilitates replacement of floss 22 by the removal of the retention means (beads) from the tips of arms 16, 20 or the un-tensioned maneuvering of the floss 22 in the embodiment shown.

Figure 3A:
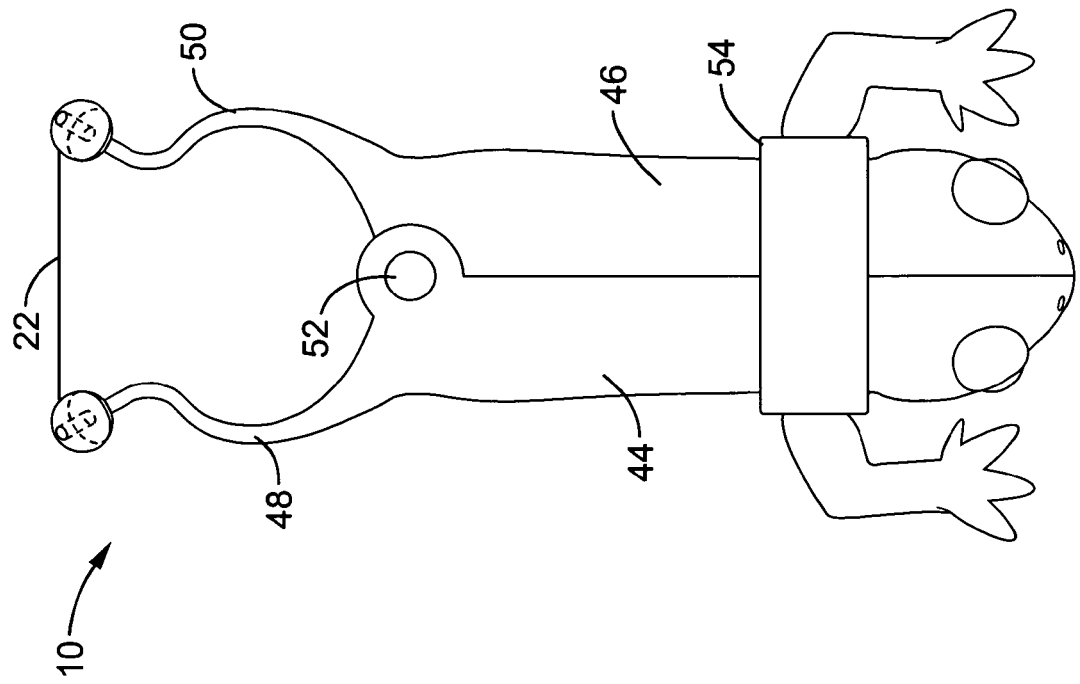
FIG. 3A is a front view of a dental flossing apparatus according to another embodiment of the present invention, showing the frog-shaped flosser apparatus in the open and unlocking position.
Figure 3B:
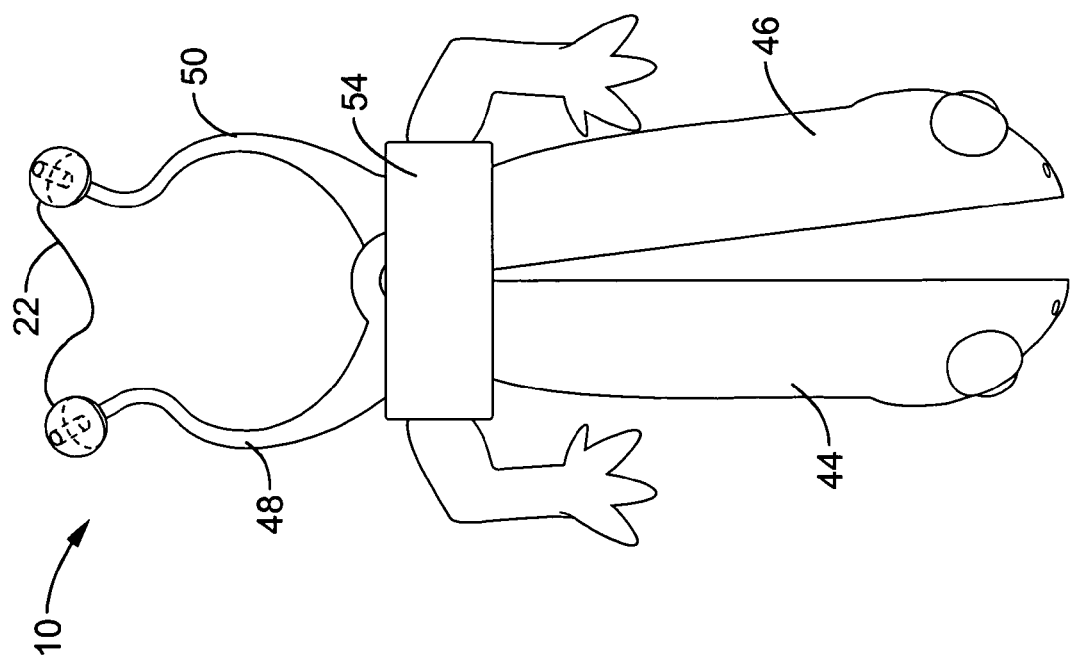
FIG. 3B is a front view of the dental flossing apparatus of FIG. 3A, shown in the closed and locked position.

FIG. 3A and FIG. 3B illustrate an example of another embodiment of the dental flossing apparatus 10 having the form of a frog. It will be appreciated that the invention may be embodied in a number of alternative entertaining shapes, such as action figures, animals, characters, or objects and so forth without departing from the teachings of the present invention. First leg 44 and second leg 46 are preferably shaped such that when brought together they form the body shape or torso of a frog, or other animal, character, object or entertaining shape. First leg 44 and arm 48 are pivotally coupled to second leg 46 and second arm 50 through a pivot pin 52. Movement of legs 44, 46 will exert tension on the length of floss 22 through first second arms 48, 50 if brought toward one another, and tension is released on floss 22 as the legs are drawn apart.

Referring to the figure, a locking means is preferably provided, such as comprising a sleeve 54 encircling legs 44 and 46. It can be seen that sleeve 54 can slide along down legs 44, 46 when they are brought together and the apparatus is in the closed position. Legs 44, 46 are preferably slightly tapered at the proximal end so that locking sleeve 54 frictionally engages and locks legs 44, 46 together when the sleeve is near the distal end of the legs 44, 46. A portion of the action figure, animal, character, or object figure may extend from the locking means, wherein the appearance of the animal/character may change in response to locking or unlocking. For example upon engaging the locked position, such as by sliding locking sleeve 54 into the locked position, the desired overall appearance of an animal, character, or object is obtained, for instance the frog as shown in FIG. 3B.

FIG. 4A and FIG. 4B illustrate an example embodiment utilizing another form of animal/character shape and an alternative locking mechanism. In this embodiment, first leg 56 and first arm 58 are pivotally coupled with second leg 60 and second arm 62 through a pivot pin 64. In this embodiment locking clasp 68 engages the distal end of legs 56, 60, and is preferably movably coupled to a first leg, and configured to lockably engage the second leg. By way of example first leg 56 is shown with locking clasp 68 having the shape of a pair of shoes and the legs 56, 60 representing human legs (or characterized legs) in the embodiment shown. When legs 56, 60 are brought together, clip 68 pivots about pin 70 and engages the distal end of leg 60 in a section 72 shaped like a human heel. Engagement may be according to friction, engagement notches, tabs, or any convenient mechanism known in the art.

Figure 6:
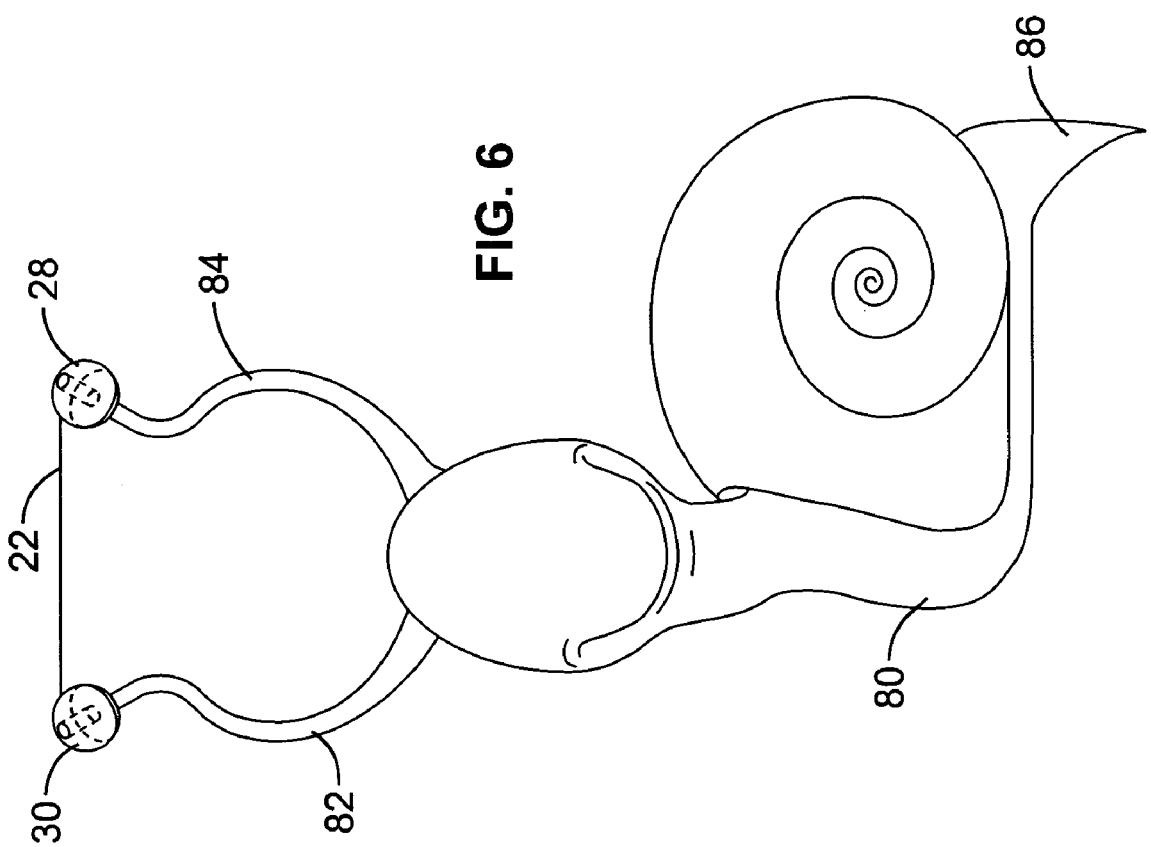
FIG. 6 is a front view of an unarticulated dental flossing apparatus according to another embodiment of the present invention, shown with a character icon handle (snail) from which extend resilient tension arms.
Figure 5:
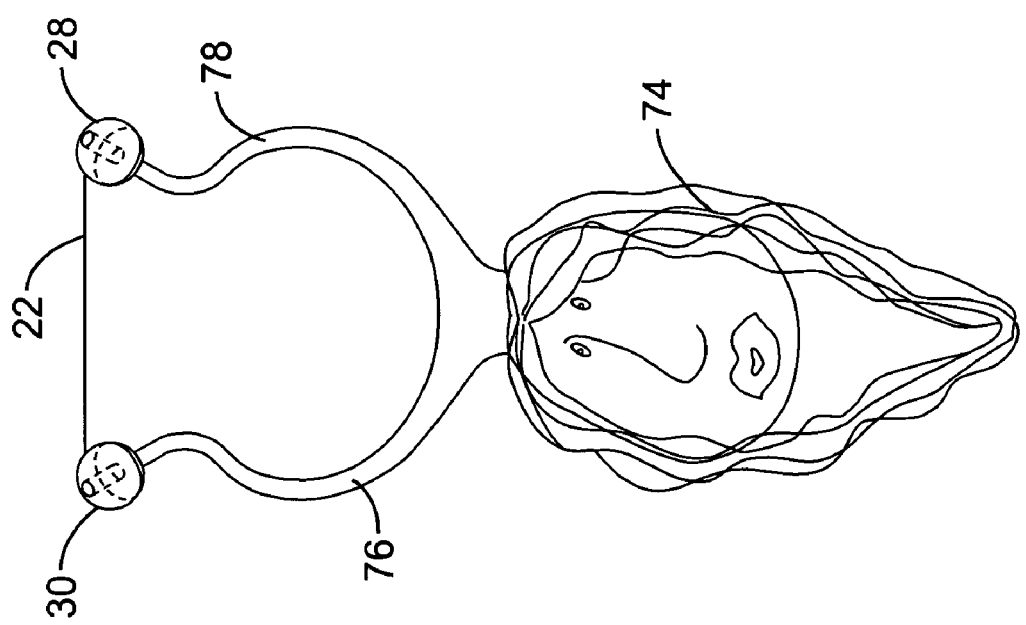
FIG. 5 is a front view of an unarticulated dental flossing apparatus according to another embodiment of the present invention, shown with a character icon handle (head) from which extend resilient tension arms.

FIG. 5 and FIG. 6 illustrate embodiments of the flosser apparatus of the present invention shown with non-articulated arms. It will be appreciated that this embodiment, as well as the previous embodiments, can be associated with a promotional advertising jingle or phrase to promote use and sale of the apparatus, with the overall shape of the apparatus being preferably selected to contribute to the trade dress and commercial impression of the apparatus.

In the figure, non-articulated resilient arms extend from the body of the flosser. The body of the apparatus may have a thematic design, exemplified as head shape 74 in FIG. 5, or an animal, character, or object body shape, such as the snail 80 of FIG. 6. The body 74 preferably has a pair of resilient arms 76, 78 that are configured to hold a length of dental floss 22 at the tips of the arms. In the embodiment shown, tension is exerted on floss 22 by resilient arms 76, 78 and floss beads 28, 30.

Referring to FIG. 6, it should be appreciated that body 80 of the apparatus in this embodiment can take essentially any shape. Further, resilient arms 82, 84 can be incorporated into the object design, such as the ears of a rabbit or other animal or antenna of an insect (not shown). Resilient arms 82, 84 may be drawn slightly toward one another for placing floss beads 28, 30 on the tips of the resilient arms. Tension is exerted on floss 22 when arms 82, 84 return to their original position. An optional pick or gum massager 86 may also be incorporated into the body of the flosser to provide added functionality.

FIG. 7A and FIG. 7B illustrate an example of floss configured with retention means along its length for tensioned engagement upon the flosser devices exemplified within the present invention. The retention means may be adapted at the ends of precut short sections of floss, or along an extended portion of floss, from which only one section is utilized at a given time. In this embodiment, the floss beads 88 are configured with a generally hemispherical shape having a retention aperture, such as central bore 90, for engaging an end portion of the tension arm, or receptacle. Floss beads 88 are attached to dental floss 92, such as at predetermined distances along the length of dental floss 92, for example configured to be separated between adjacent beads into segments. In the embodiment shown in FIG. 7A and FIG. 7B, the floss beads 88 are configured to fit on a correspondingly shaped tip 94 of an arm. The receptacle on tip 94 is exemplified as a post 95 that is sized and shaped to fit bore 90 of floss bead 88. The linear distance between beads 88 along floss 92 can be adjusted to fit apparatus of varying sizes. It should be appreciated that the retention means along the length of floss 92 may be adapted for retention upon the flossing apparatus utilizing any convenient retention mechanism.

FIG. 8A through FIG. 12B illustrate that post and bore mounting may be adapted in any number of alternative shapes for retaining the dental floss between the arms of the dental flossing apparatus. In FIG. 8A through 11B the shape of the post and bore is shown adapted to different shapes. In FIG. 12A, 12B, the shape of the bead itself is adapted to different shapes. It should also be appreciated that the post shape need not match the bore shape, insofar as the post can be inserted through the bore. For example, an octagonal post can be inserted into a square bore of a sufficient size, although this is generally less preferred. In the embodiment shown in FIG. 8B, the central bore 96 of the bead 97 is triangular in shape. Bead 98 has a central bore 100 with a hexagonal shape as seen in FIG. 9A and FIG. 9B. In FIG. 10A and FIG. 10B bead 102 has a star shaped central bore 104. A square shaped bore 106 in bead 108 is seen in the embodiment shown in FIG. 11A and FIG. 11B. It can be seen that the non-circular geometric cross section of the post and central bores shown in FIG. 8A through FIG. 11B will preferably eliminate any axial rotation around the post on the tip of the arms when forces are applied on the floss during use. It should be appreciated that the bore and post shapes may be selected from the group of geometric shapes consisting of circles, ovals, triangles, trapezoids, squares, rectangles, polygons, pentagons, hexagons, heptagons, octagons, and other shapes which would be obvious in view of these teachings. Bore and post shapes can be symmetrical or unsymmetrical and can represent other shapes such as various stars shapes, a heart, crescent or cross. Furthermore, multiple engagement structures may be utilized to couple a floss bead to the end portion of a tension arm, such as multiple posts, pins, bores, notches, sockets, and so forth.

Although the hemispherical shaped bead is generally preferred, the bead 110 may assume other shapes, for example the generally "ring" or "donut" shaped bead 110 as seen in FIG. 12A and FIG. 12B, having central bore 112 exemplified as a circular bore.

Figure 13:
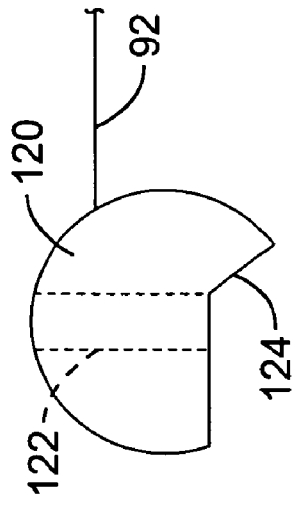
FIG. 13 is a side view of a floss bead with a beveled bottom surface that engages a corresponding surface on the tip of the tension arm according to an aspect of the present invention, shown with the central bore through the bead for retention on the flossing arm.
Figure 14:
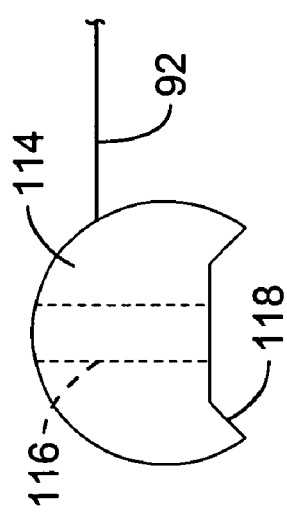
FIG. 14 is a side view of a floss bead with an angled bottom surface that engages a corresponding surface on the tip of the tension arm according to an aspect of the present invention, shown with the central bore through the bead for retention on the flossing arm.

FIG. 13 through FIG. 14 illustrate that the implementation of post and bore retention means need not be limited to spherical or planar implementations. The bottom surface of the floss beads and the corresponding surface of the tip of the arms of the apparatus may alternatively be non-planar. In FIG. 13, bead 114 has a central bore 116 and a bottom surface 118 that has preferably beveled edges. The bead 114 is configured to engage and seat on a post and surface of a tip of an arm that is similarly configured. Bottom surface 118 could also have perpendicular edges (not shown).

FIG. 14 illustrates another similar bead 120 configuration with a central bore 122 and lower surface 124 with a single beveled edge. It will be seen that the configurations shown in FIG. 13 and FIG. 14 reduce the force exerted on the post of the tip of the arms when tension is created in the floss by distributing the force across the beveled surfaces of the tip in addition to the post.

It should be appreciated that the post and/or the bore can be adapted to alter the force required to install or remove the bead from the tip of the flosser arm. One preferred configuration of this is the use of snap-on beads for engaging the posts (not shown). For example, a protrusion along the tip of the post can be configured to retain the bead once the post is inserted through the bead, or protrusions along a median portion of the post may engage an interior recess (i.e. recessed ring) as the post is pressed into the bead. The protrusion preferably comprises one or more annular ridges disposed at the distal portions of the posts to prevent inadvertent disengagement of the beads. The head of the post may also be configured with flexible portions (detents) for engaging a portion of the bead, such as an end which is split into two or more compliant segments having an exterior structure to engage the bead.

Figure 15A:
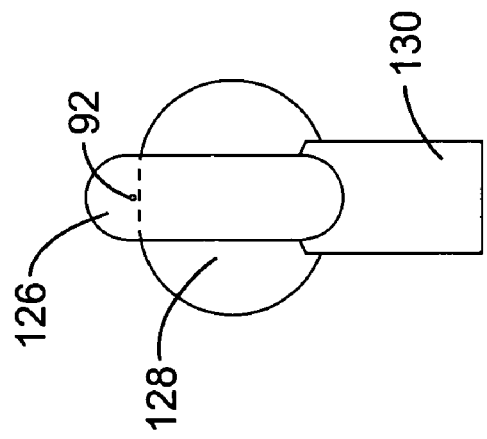
FIG. 15A is a front view of an annular floss bead that affixes to the spherical tip of a tension arm according to another aspect of the present invention, shown with a partial annular ring section engaged over the exterior of the tension arm tip.
Figure 15B:
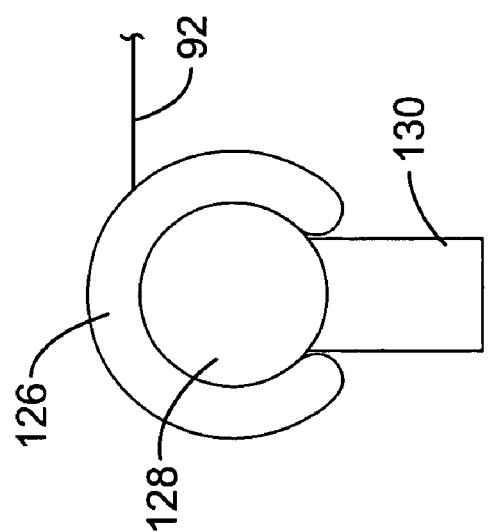
FIG. 15B is a side view of the annular floss bead of FIG. 15A.

FIG. 15A and FIG. 15B illustrate that the floss retention means need not be configured as a post and bore. A floss bead 126 is visible which is adapted for being retained over a portion of an exterior of the tip, for example generally having a "C" shape and sized to fit over the tip 128, preferably spherical, of an arm 130 of the apparatus. In a further embodiment, (not shown) the floss beads may also be hemispherical or "cup" shaped and sized to engage the spherical tip of an arm.

Figure 16:
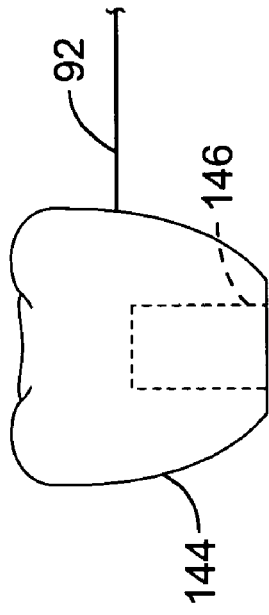
FIG. 16 is a front view of a floss bead according to an aspect of the invention in the shape of a heart.
Figure 17:
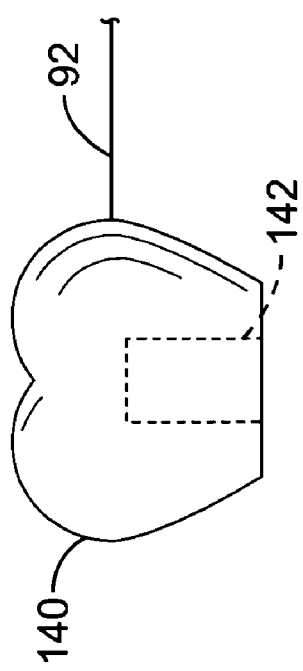
FIG. 17 is a front view of a floss bead according to an aspect of the invention in the shape of a tooth.
Figure 18:
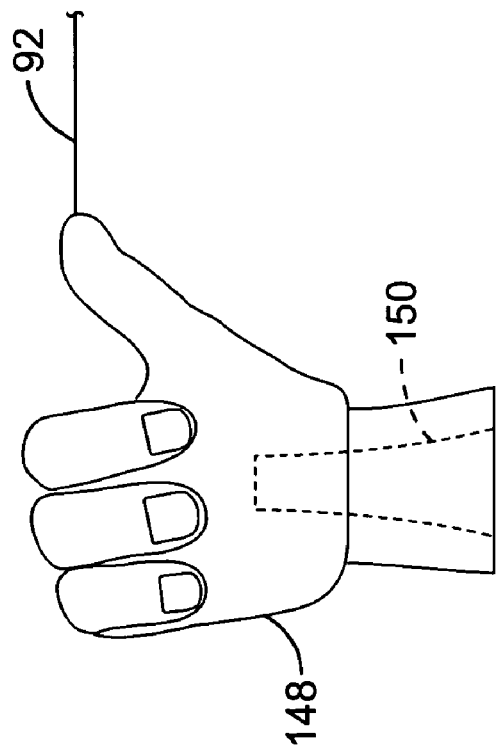
FIG. 18 is a front view of a floss bead according to an aspect of the invention in the shape of a hand.

FIG. 16 through FIG. 18 illustrate that the floss retention means may be configured as a recognized object independent of the flosser or as part of the flosser design.

Figure 19:
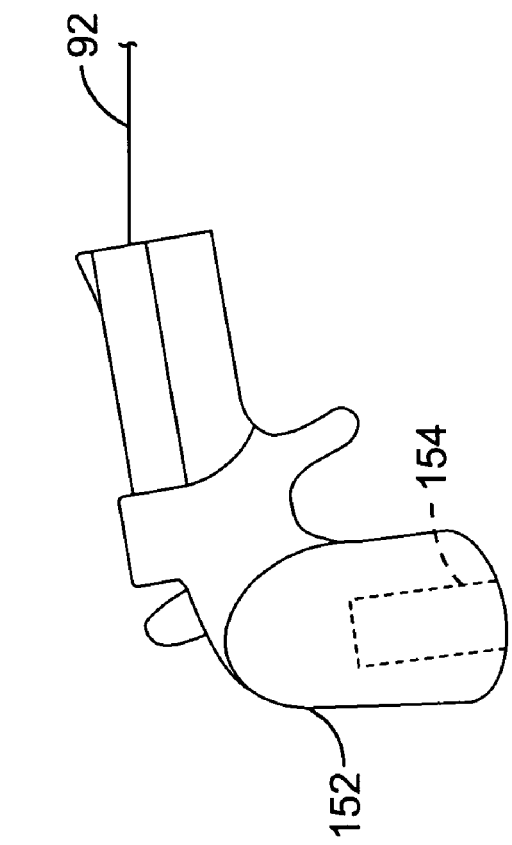
FIG. 19 is a front view of a floss bead according to an aspect of the invention in the shape of a gun.

FIG. 16 illustrates a heart shaped floss bead 140 with a central bore 142 and coupled to floss 92. FIG. 17 illustrates a molar shaped floss bead 144 with a central bore 146. In FIG. 18 a hand, fist or glove 148 is coupled to floss 92 at the thumb and has a central bore 150 to mate to a corresponding post, preferably shaped as arms (not shown). In FIG. 19 a gun 152 is illustrated with floss 92 coupled at the barrel of the gun and a central bore 154 in the handle. Other object shapes such as fruits and vegetables, sports balls such as baseballs, pool balls, bowling balls, soccer balls or footballs, sports helmets with team logos such as football or hockey, and military gear such as helmets, knives, hand grenades, bombs, guns etc. may be represented in the floss retention means.

Figure 20:
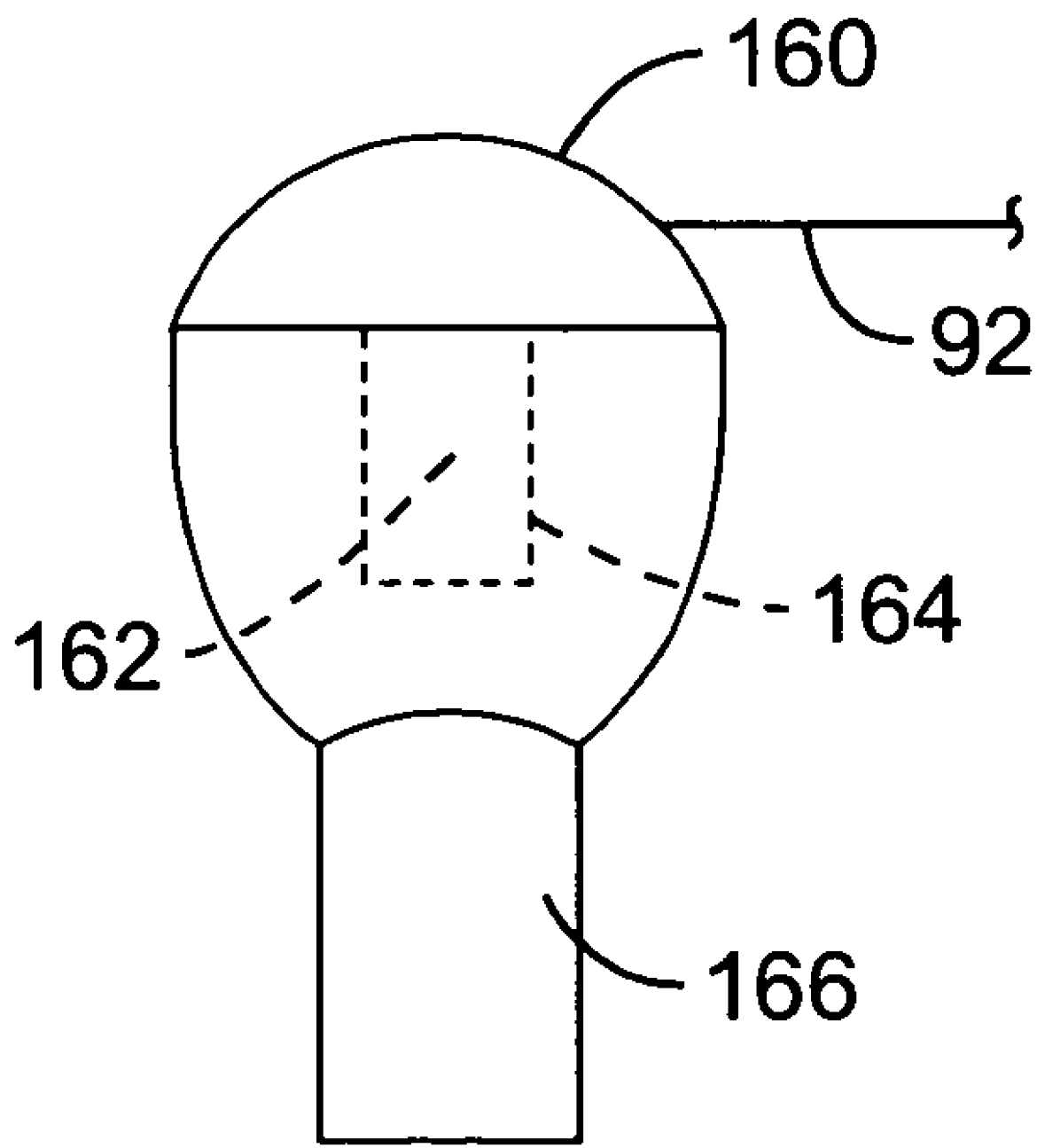
FIG. 20 is a front view of an annular floss bead according to another aspect of the present invention, shown with a post that fits within a corresponding sleeve in the tip of a tension arm.

FIG. 20 illustrates by way of example another post-style embodiment, wherein the roles of the post and bore are reversed. The floss bead 160 incorporates a post 162 which is configured for receipt in a socket 164 within tip 166 of the arm of an apparatus. While a cylindrical post and socket are shown in the figure, it will be understood that post 162 and corresponding socket 164 could be adapted to have any geometrical cross section such as described in FIG. 8A through FIG. 12B. Further, floss bead 160 can be configured to any shape such as described in FIG. 8A through FIG. 19.

Figure 21A:
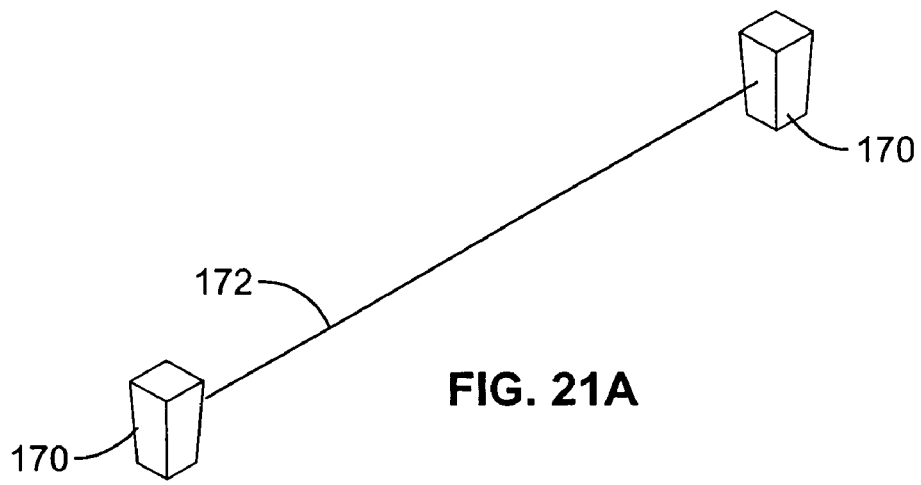
FIG. 21A is a front perspective view of a beaded floss section according to another aspect of the present invention, shown configured to fit within a sleeve in the tip of a tension arm.
Figure 21B:
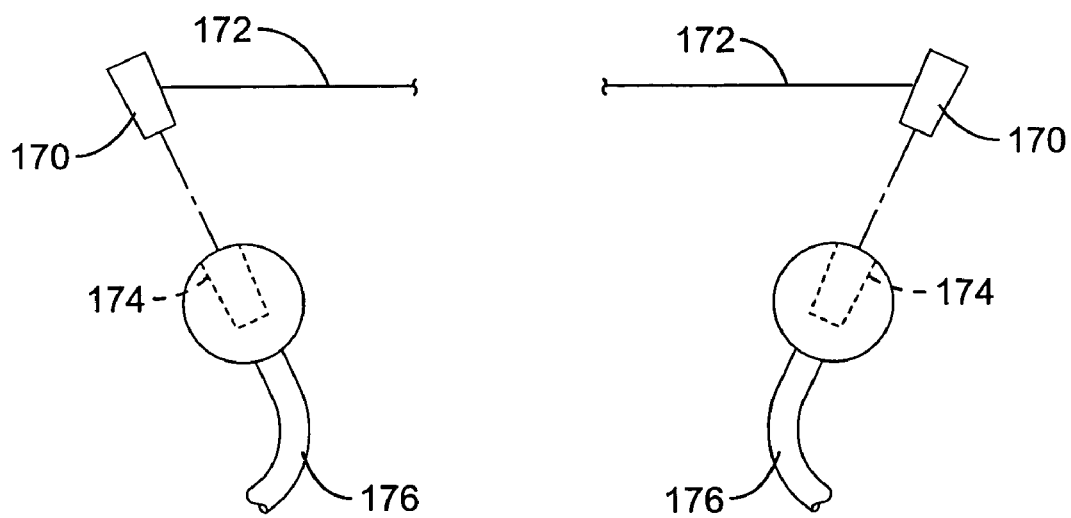
FIG. 21B is a side view of the beaded floss section of FIG. 21A, shown aligned over the tips of the tension arms prior to placement within the sleeves.
Figure 21C:
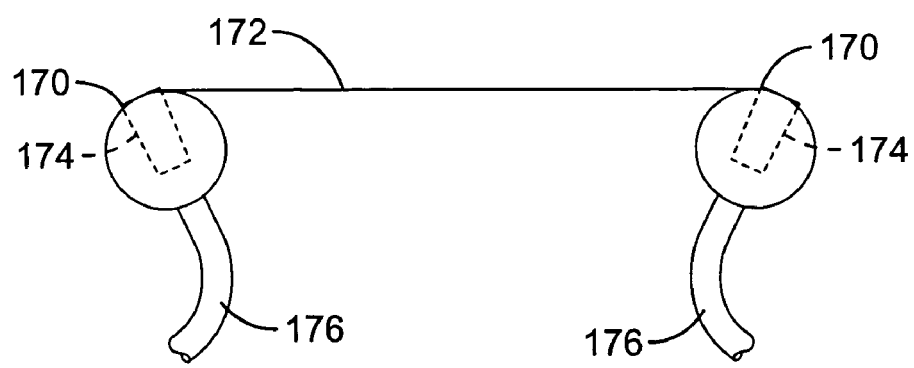
FIG. 21C is a side view of the beaded floss section of FIG. 21B, shown after engagement of the floss section with the tension arms.

FIG. 21A through FIG. 21C illustrate a still further example of a floss retention means on the tips of the flossing device. In this embodiment the floss beads are configured for insertion within the tips of the flossing device, for example elongated beads 170 (i.e. rectangular, cylindrical or other geometric cross section) are configured with a length of floss 172 for insertion into socket 174 on arms 176. The embodiment shown may also be adapted utilizing shortened cylindrical sections, such as a cubed bead within the socket of tension arms 176. In a preferred embodiment, elongated beads 170 are tapered and socket 174 has a corresponding taper to facilitate removal. It can be seen that tension arms 176 are positioned so that the beads 170 can be inserted into sockets 174 in the tips of the tension arms 176 as seen in FIG. 21B. Tension is exerted on the length of floss 172 when the tension arms are drawn apart as seen in FIG. 21C. Although a tapered rectangular prism shaped bead was used in FIG. 21A through 21C, it will be understood that other shaped beads such as truncated pyramids and cones may be used as well. It should be recognized that means for facilitating the removal of the beads from the tension arms may be incorporated, such as recesses, and/or protrusions for manual release of the beads, or the use of structures, recesses, or apertures to be engaged by a bead removal element, such as extending from the package of beaded floss. Preferably the beads may be removed by applying sufficient tension force on the floss in a given direction, and/or applying manual pressure thereto, to release the bead from the tip of each flossing arm.

Figure 22:
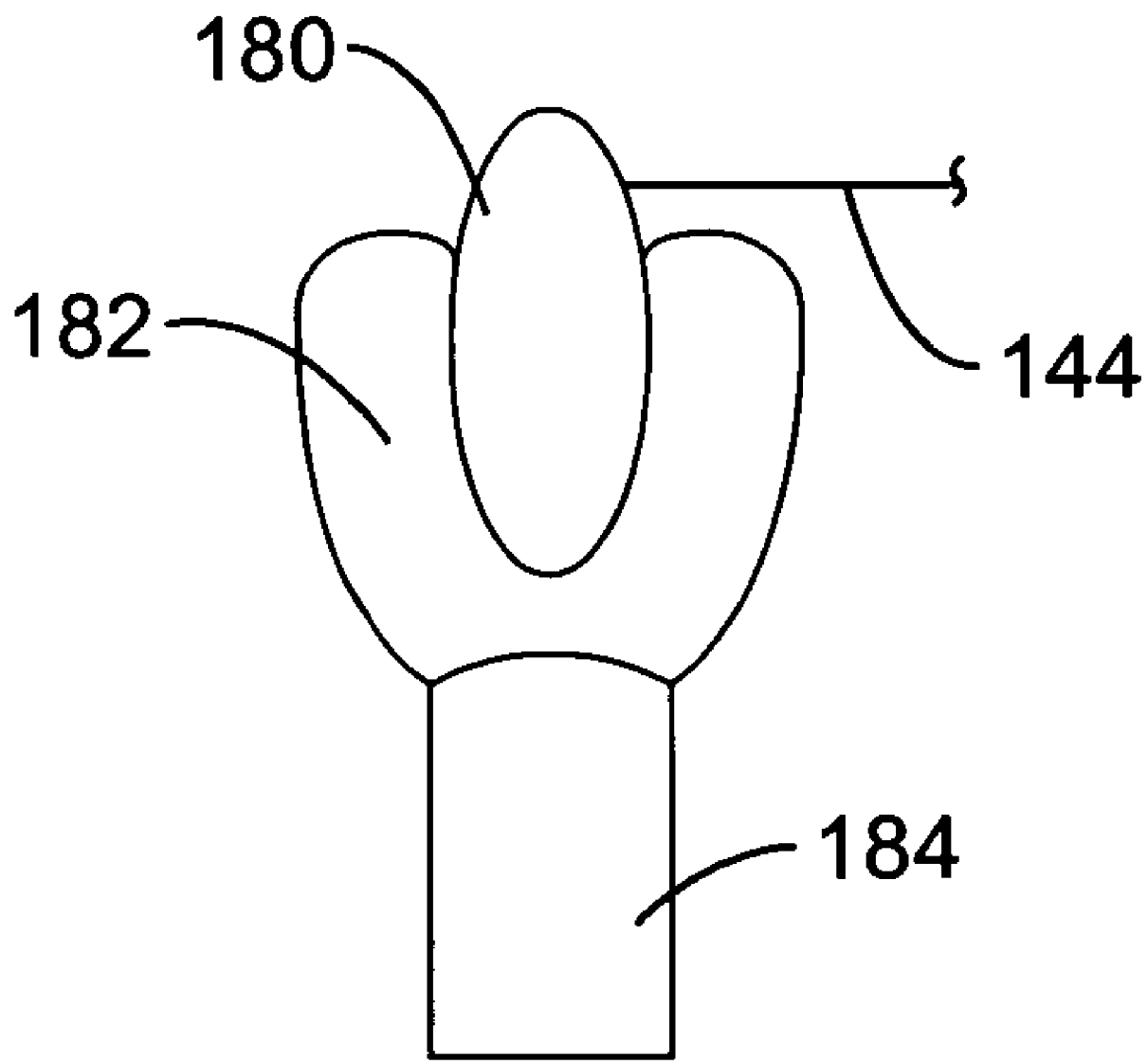
FIG. 22 is a front view of a floss bead according to another aspect of the present invention, shown having a disk shape that fits within a corresponding groove in the tip of a tension arm.

FIG. 22 illustrates another example of a floss bead 180, herein depicted as disk shaped which is configured to fit within a notch or groove in the tip 182 of tension arm 184. Removal of floss bead 180 can be accomplished by sliding the bead laterally through the groove in tip 182.

Figure 23B:
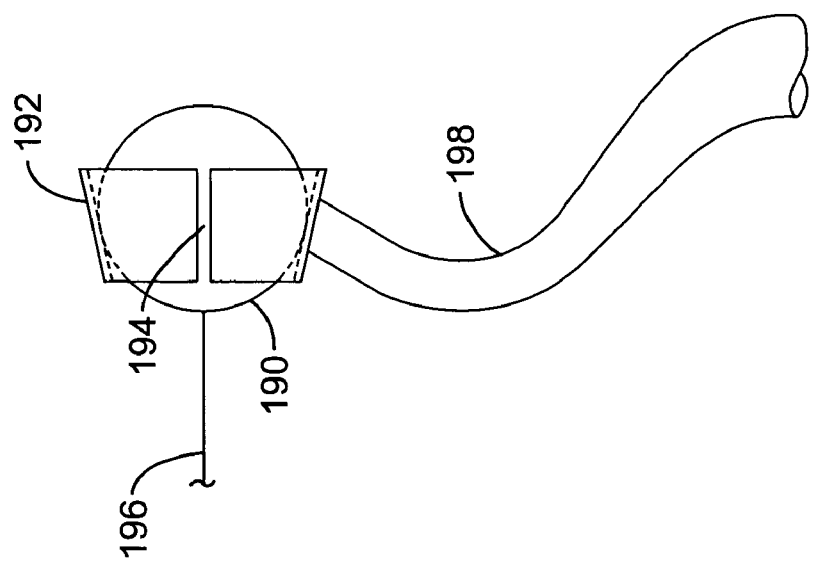
FIG. 23B is a detail view of the tension arm tip of FIG. 23A, showing engagement between the tip and bead.
Figure 23A:
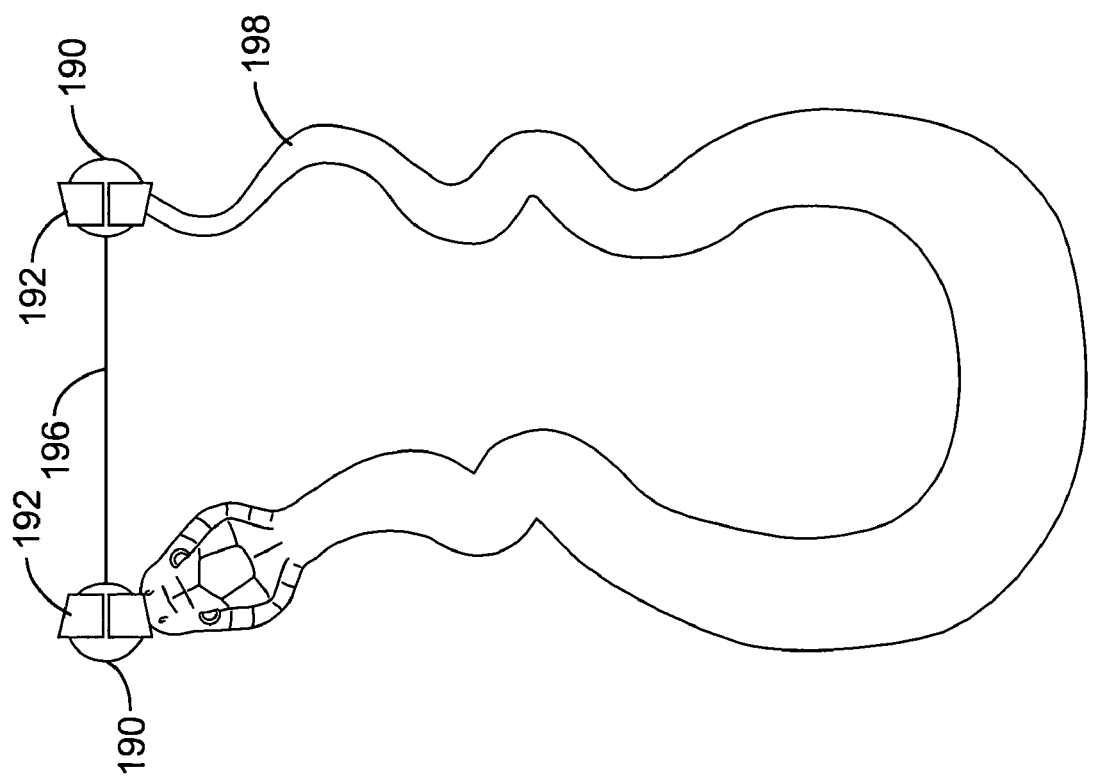
FIG. 23A is a front view of a dental flossing apparatus according to an aspect of the present invention, shown in the shape of a snake having frustoconical rings at the tips of the tension arms for retaining the floss beads.

FIG. 23A and FIG. 23B illustrate a further example of a bead and holder configuration, shown depicting a generally spherical floss bead 190 retained in a frustoconical collar 192. This arrangement can be generally referred to as a ball-and-socket engagement structure. The collar 192 preferably has a gap 194 (shown in FIG. 23B) to allow the passage of dental floss 196 when loading the beaded dental floss segments onto the tips of tension arms 198. Collar 192 is positioned horizontally at the tip of each tension arm 198 and the narrower opening of one collar 192 is preferably oriented toward the other collar 192. It can be seen that loading of the floss segments, requires that after inserting a first bead into collar 192, that tension arms 198 be brought sufficiently close together to allow inserting the floss through gaps 194 so that the second bead may engage the second collar 192. Tension is exerted on floss 196 as the compression forces on tension arms 198 is released.

Figure 24:
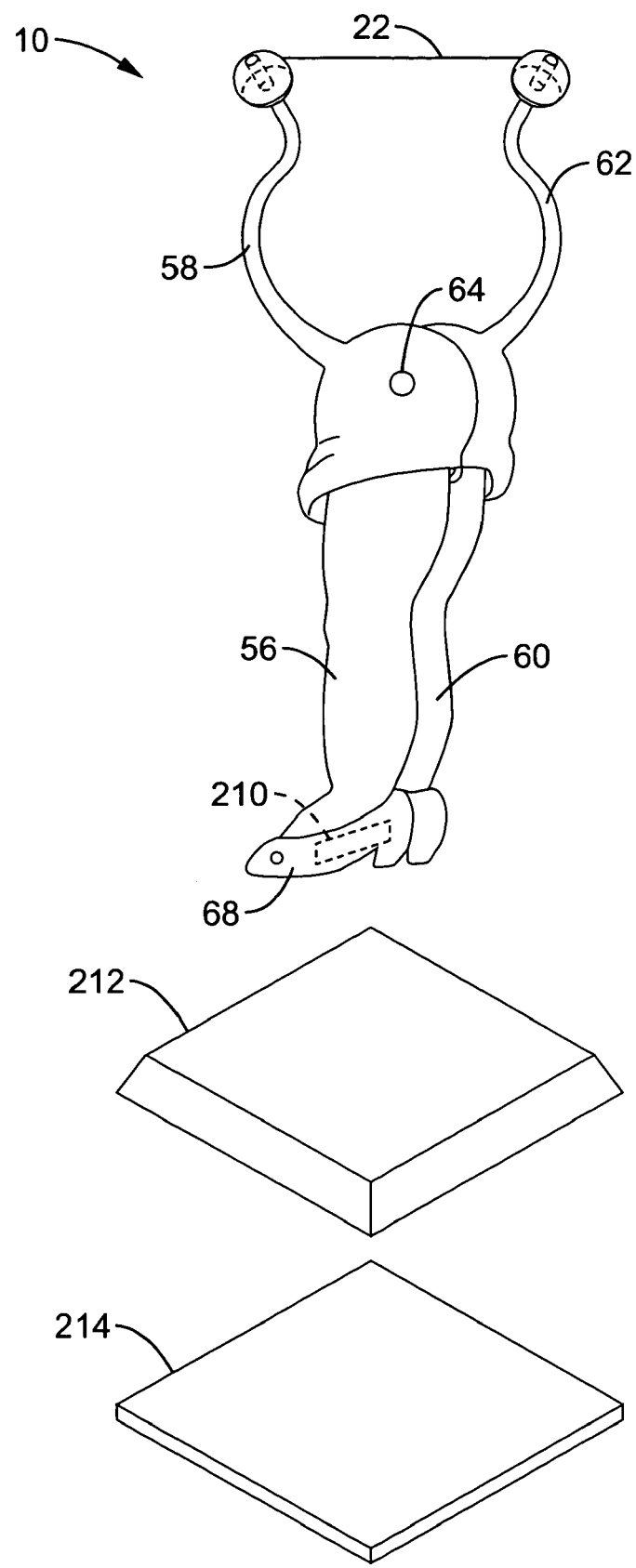
FIG. 24 is an assembly view of a dental flossing apparatus as previously shown in FIG. 4A and configured with a magnet to affix to a base having iron metal.

FIG. 24 illustrates a disassembled view of a support base for a flossing apparatus 10 previously shown in FIG. 4A. Locking clasp 68 has imbedded magnets 210. A plastic base 212 has a plate of iron metal 214 coupled beneath. When flossing apparatus 10 is placed on plastic base 212, the attraction of magnet 210 and metal plate 214 supports flossing apparatus 10 in a standing position. In further embodiments, iron metal is substituted for imbedded magnets 210 and/or a magnet is substituted for base metal 214. In a still further embodiment, imbedded magnet 210 will support flossing apparatus 10 on a porcelain or enamel sink or plumbing fixture having an iron metal base.

In another embodiment (not shown) a suction cup is attached to the bottom of locking clasp 68 that will couple to base 212 or to the top of a sink or smooth counter top to support flossing apparatus 10.

The embodiments of the present invention may be fabricated from any convenient easily cleaned material. A preferred group of materials for the device are thermal formed (i.e. molded) polymers (plastics) which provide simple low cost fabrication while being easily cleaned and sanitized. It should be appreciated, however, that materials such as resins, metals, and other easily cleaned materials may be utilized.

It should be noted that the invention specification, and in particular the detailed description of embodiments, are provided by way of illustrative example. Therefore, it will be recognized that the invention may be practiced according to any combination (i.e. superset, subset, mixed combination) of inventive aspects described, or in combination with that which is known in the art, without departing from that which is taught within the present invention. Consequently, there is no need for the application to recite each possible variant which may be practiced, however, these variants are still considered to be taught by the present invention. For example, the floss retention means described may be combined any of the various floss device handle configurations without departing from the invention. Additionally, each of the handles may be adapted in the shape of other animals, characters, action figures or objects, without departing from the present invention. Furthermore, the different means of reversibly coupling the dental floss may be utilized on each retention arm.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for flossing teeth, comprising:
a first leg;
a first arm extending from said first leg;
a second leg pivotally coupled to said first leg;
a second arm extending from said second leg;
means for reversibly coupling a length of dental floss for retention between said first and second arms under sufficient tension, applied by drawing said first and said second legs toward one another, for being manipulated between the teeth of a user during flossing;
wherein said means for reversibly coupling said length of dental floss comprises a first bead and a second bead coupled to a length of dental floss; and
means for reversibly coupling each said bead with each said arm of said apparatus;
wherein said means for reversibly coupling a bead to an arm comprises a post mounted to the tip of said arm and configured of a size and shape to be disposed within a bore within said bead; and
wherein said posts have non-circular cross sections which restrict rotation of said beads around said posts.

2. An apparatus as recited in claim 1, further comprising:
means for reversibly locking said first leg and said second leg together;
wherein said first arm and said second arm exert a tension force on said length of dental floss.

3. An apparatus as recited in claim 2, wherein said means for reversibly locking said first leg and said second leg comprises:
a slidable sleeve configured to engage at least a portion of said first leg and said second leg and further configured to slide between a locked position and an unlocked position.

4. An apparatus as recited in claim 2
wherein said means for reversibly locking said first leg with said second leg comprises a clasp coupled to said first leg;
wherein said clasp is configured to engage and prohibit the pivotal movement of said second leg.

5. An apparatus as recited in claim 4
wherein said clasp comprises a clip pivotally coupled to said first leg; and
wherein said clip is configured to frictionally engage said second leg and prohibit movement of said second leg.

6. An apparatus as recited in claim 5, wherein said clip is configured to frictionally engage a corresponding structure in said second leg.

7. An apparatus as recited in claim 6, wherein said clip further comprises a magnet coupled to said clasp and configured to reversibly couple said clip to a magnetic object.

8. An apparatus for flossing teeth, comprising:
a first leg;
a first arm extending from said first leg;
a second leg pivotally coupled to said first leg;
a second arm extending from said second leg;
means for reversibly coupling a length of dental floss for retention between said first and second arms under sufficient tension, applied by drawing said first and said second legs toward one another, for being manipulated between the teeth of a user during flossing; and
wherein said means for reversibly coupling said length of dental floss comprises:
a first bead and a second bead coupled to a length of dental floss; and
means for reversibly coupling each said bead with each said arm of said apparatus; and
wherein said means for reversibly coupling a bead to an arm comprises a post mounted to the tip of said arm and configured of a size and shape to be disposed within a bore within said bead; annular ridges disposed at distal portions of said post to prevent inadvertent disengagement of said bead from said post.

9. An apparatus as recited in claim 8, wherein said means for reversibly coupling a bead to an arm comprises a post extending from said bead configured of a size and shape for being received within a bore proximal to the tip of said arm.

10. An apparatus as recited in claim 9, wherein said posts have a cross-section selected from the group of shapes consisting essentially of circles, ovals, triangles, trapezoids, squares, rectangles, polygons, pentagons, hexagons, heptagons, octagons, star, heart, crescent and a cross.

11. An apparatus as recited in claim 8, wherein said means for reversibly coupling each said bead with each said arm comprises:
a shaped bead joined along a length of dental floss; and
a notch proximal the tip of said arm configured for receiving said shaped bead.

12. An apparatus for flossing teeth, comprising:
a first leg;
a first arm extending from said first leg;
a second leg pivotally coupled to said first leg;
a second arm extending from said second leg: and
means for reversibly coupling a length of dental floss for retention between said first and second arms under sufficient tension, applied by drawing said first and said second leas toward one another, for being manipulated between the teeth of a user during flossing;
wherein said means for reversibly coupling said lenath of dental floss comprises:
a first bead and a second bead coupled to a length of dental floss; and
means for reversibly coupling each said bead with each said arm of said apparatus;

wherein said means for reversibly coupling each said bead to each said arm comprises:
a shaped bead joined to a length of dental floss; and
a socket proximal the tip of said arm configured to receive said shaped bead;
wherein said socket is shaped as an open frustoconical sleeve; and
wherein said socket is configured with a slot through which said dental floss may be passed for aligning said shaped bead with the interior of said socket.

13. An apparatus as recited in claim 12, wherein said means for reversibly coupling each said bead to each said arm comprises:
at least a first and second bead coupled to a length of dental floss; and
a spherical tip proximal each said arm configured to frictionally engage each said bead.

14. An apparatus as recited in claim 12, further comprising:
means for reversibly locking said first leg and said second leg together;
wherein said first arm and said second arm exert a tension force on said length of dental floss.

15. An apparatus as recited in claim 14, wherein said means for reversibly locking said first leg and said second leg comprises:
a slidable sleeve configured to engage at least a portion of said first leg and said second leg and further configured to slide between a locked position and an unlocked position.

16. An apparatus as recited in claim 14
wherein said means for reversibly locking said first leg with said second leg comprises a clasp coupled to said first leg;
wherein said clasp is configured to engage and prohibit the pivotal movement of said second leg.

17. An apparatus as recited in claim 16
wherein said clasp comprises a clip pivotally coupled to said first leg; and
wherein said clip is configured to frictionally engage said second leg and prohibit movement of said second leg.

18. An apparatus as recited in claim 17, wherein said clip is configured to frictionally engage a corresponding structure in said second leg.

19. An apparatus as recited in claim 18, wherein said clip further comprises a magnet coupled to said clasp and configured to reversibly couple said clip to a magnetic object.

20. An apparatus for flossing teeth, comprising:
a first leg;
a first arm extending from said first leg;
a second leg pivotally coupled to said first leg;
a second arm extending from said second leg; and
means for reversibly coupling a length of dental floss for retention between said first and second arms under sufficient tension, applied by drawing said first and said second lees toward one another, for being manipulated between the teeth of a user during flossing;
wherein said means for reversibly coupling said length of dental floss comprises:
a first bead and a second bead coupled to a length of dental floss; and
means for reversibly coupling each said bead with each said arm of said apparatus; and
wherein said beads are configured in a shape selected from the group of shapes consisting of a heart, a tooth, a hand, a fruit, a vegetable, a sports ball, a sports helmet, a knife, a hand grenade, a bomb, or a gun.

* * * * *